United States Patent [19]
Ishida et al.

[11] Patent Number: 5,589,465
[45] Date of Patent: Dec. 31, 1996

[54] GLYCOLIPID DERIVATIVES ACTING AS LIGANDS FOR SELECTINS

[75] Inventors: Hideharu Ishida, Gifu; Makoto Kiso, Motosu-gun; Akira Hasegawa, 1735-160 Kano, Gifushi, Gifu-ken, all of Japan

[73] Assignees: Akira Hasegawa; Kanebo Ltd., both of Japan

[21] Appl. No.: 396,793

[22] Filed: Mar. 1, 1995

[30] Foreign Application Priority Data

Sep. 30, 1994 [JP] Japan .................................. 6-261557

[51] Int. Cl.6 .......................... A61K 31/70; C07H 3/06; C07H 11/00; C07H 15/04
[52] U.S. Cl. .................. 514/25; 514/61; 536/4.1; 536/17.2; 536/18.4; 536/118; 536/119; 536/122
[58] Field of Search .................. 536/17.2, 4.1, 536/18.4, 118, 119, 122; 514/25, 61

[56] References Cited

U.S. PATENT DOCUMENTS

| | | | |
|---|---|---|---|
| 5,440,015 | 8/1995 | Macher et al. | 530/329 |
| 5,444,050 | 8/1993 | Kogan et al. | 514/25 |
| 5,460,945 | 10/1995 | Springer et al. | 435/7.24 |

FOREIGN PATENT DOCUMENTS

| | | | |
|---|---|---|---|
| 0579196 | 1/1994 | European Pat. Off. | |
| 93/10796 | 6/1993 | WIPO | |
| 94/00477 | 1/1994 | WIPO | |

OTHER PUBLICATIONS

Hasegawa et al. *J. Carbohydrate Chem.* 1993, 12(8), 1203–1216.

*Primary Examiner*—Gary E. Hollinden
*Assistant Examiner*—Kathleen Kahler Fonda
*Attorney, Agent, or Firm*—Millen, White, Zelano & Branigan, P.C.

[57] ABSTRACT

Novel glycolipid derivatives of Formula (I):

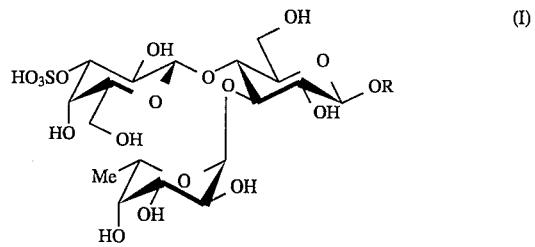

wherein R is a long chain alkyl, or their salts are disclosed. These compounds act as a ligand for selectin family and exhibit a remarkable inhibitory effect on the binding of selectin family to its native ligand sialyl Lewis$^x$.

9 Claims, 1 Drawing Sheet

GLYCOLIPID DERIVATIVES ACTING AS LIGANDS FOR SELECTINS

FIELD OF THE INVENTION

The present invention relates to novel glycolipid derivatives acting as a ligands for selectins. It also relates to a pharmaceutical composition comprising said glycolipid derivatives and to methods of using them.

BACKGROUND OF THE INVENTION

Recent studies indicated the involvement of selectin-oligosaccharide interactions in various inflammatory disease. It is known that E-selectin (ELAM-1), P-selectin (GMP-140) or L-selectin (LECAM-1) plays an important role in the migration of inflammatory cells from the blood stream to inflammatory sites. These selectin family are expressed on a variety of cell surfaces. For example, ELAM-1 is an adhesion molecule on vascular endothelial cells with inflammation. GMP-140 is an adhesion molecule expressed on platelets or vascular endothelial cells. LECAM-1 is an adhesion molecule expressed on leukocytes. These selectins are believed to be involved in a complicated manner in the progress of clinical manifestation of complicated a disease such as chronic inflammation. Attempts have been made, therefore, to find a blocker of selectins effective to inhibit their cell-adhesion activities at an early stage of inflammation. To this end, it would be desirable for the blocker to exert its cell adhesion-inhibitory effects on all members of the selectin family.

It has also been reported that various selectins are involved in ischemia-reperfusion injury accompanying invasion of neutrophils into endothelium. Buerke et al., J. Clin. Invest., 93, 1140–1148 (1994); and Okada et al., Stroke, 25, 202–210 (1994). It has also been reported that antibodies to E-selectin, P-selectin and L-selectin, respectively, attenuated ischemia-reperfusion injury in the model animals. D. Altavill et al., Eur. J. Pharmacol., 270, 45–51 (1994); R. K. Winn et al., J. Clin. Invest., 92, 2042–2047 (1993); and Xin-liang Ma et al., Circulation, 88, 649–658 (1993). Y. Seko et al. reported in Pro. Jpn. Soc. Immunol., 24, 108 (1994) a synthetic selectin oligopeptide effective in the reduction of rat myocardial ischemia-reperfusion injury. It is, therefore, believed that a blocker for cell adhesion activities of selectins is also useful in controlling ischemia-reperfusion injury.

M. L. Phillips et al. reported in Science, 250, 1130–1132 (1990) that the native ligand for ELAM-1 is sialyl Lewis$^x$ oligosaccharide. Since then a certain number of its derivatives have been reported. See, U.S. Pat. No. 5,143,712; U.S. Pat. No. 5,211,936; U.S. Pat. No. 5,211,937; U.S. Pat. No. 5,369,096; and EP-A-589556. These derivatives reported as ligands binding to ELAM-1 are oligosaccharides bearing fucose and sialic acid or a long chain alkanoic moiety in the molecule.

The present invention provides a novel glycolipid derivative which binds to any of the selectins as a ligand. The invention also provides a pharmaceutical composition for use in the prophylaxis or treatment of various inflammatory disease or reperfusion injury after ischemia comprising a pharmaceutically acceptable salt of said glycolipid derivative.

SUMMARY OF THE INVENTION

In one aspect, the present invention provides a glycolipid derivative of Formula (I):

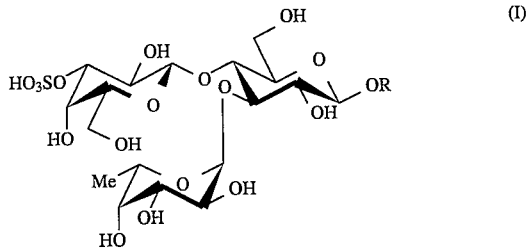

(I)

wherein R is a straight or branched alkyl having 20 to 40 carbon atoms, in the form of a pharmaceutically acceptable salt.

In another aspect, the present invention provides a novel polysaccharide derivative of Formula (III):

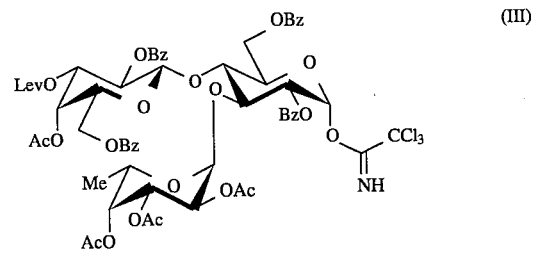

(III)

wherein Ac is acetyl, Bz is benzoyl, Lev is levuloyl and Me is methyl. The compound of Formula (III) is useful as a starting material in the synthesis of the glycolipid derivative of Formula (I).

In a further aspect, the present invention provides a pharmaceutical composition comprising a pharmaceutically acceptable salt of the glycolipid derivative of Formula (I) in admixture with a pharmaceutically acceptable carrier.

DETAILED DESCRIPTION OF THE PREFERRED EMBODIMENTS

Figure 1:
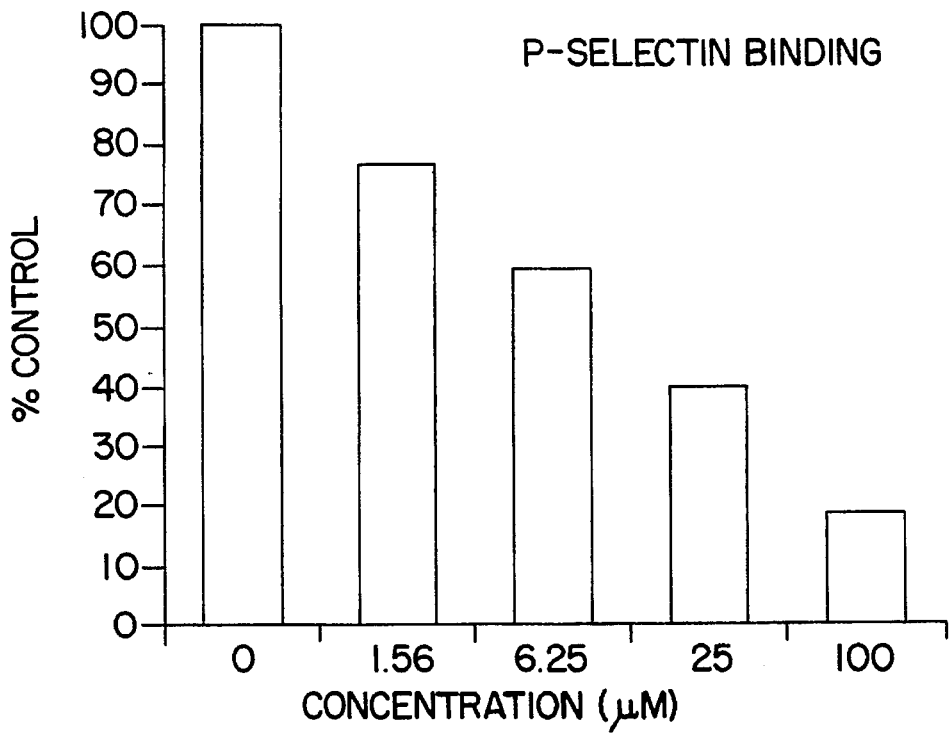
FIG. 1 is a graph showing the inhibitory effect of the glycolipid derivative of the present invention at varying concentrations on the binding of P-selectin to sialyl Lewis$^x$.

Examples of long chain-alkyls R in Formula (I) include 2-(hexyl)tetradecyl, 2-(octyl)tetradecyl, 2-(decyl) tetradecyl, 2-(dodecyl)tetradecyl, 2-(dodecyl)hexadecyl, 2-(dodecyl)octadecyl, 2-(dodecyl)eicocyl, 2-(tetradecyl) hexadecyl, 2-(tetradecyl)octadecyl, 2-(tetradecyl)eicocyl, 2-(hexadecyl)octadecyl, 2-(hexadecyl)eicocyl, 2-(octadecyl) eicocyl, 3-(hexyl)tetradecyl, 3-(octyl)tetradecyl, 3-(decyl) tetradecyl, 3-(dodecyl)tetradecyl, 3-(dodecyl)hexadecyl, 3-(dodecyl)octadecyl, 3-(dodecyl)eicocyl, 3-(tetradecyl) hexadecyl, 3-(tetradecyl)octadecyl, 3-(tetradecyl)eicocyl, 3-(hexadecyl)octadecyl, 3-(hexadecyl)eicocyl or 3-(octadecyl)eicocyl. 2-(Tetradecyl)hexadecyl is preferable among others.

Examples of cations forming a pharmaceutically acceptable salt of the glycolipid derivative of Formula (I) include inorganic metals such as sodium, potassium, calcium or magnesium, and organic bases such as arginine or lysine.

The most preferred salt of the glycolipid derivative of Formula (I) has Formula (IIa):

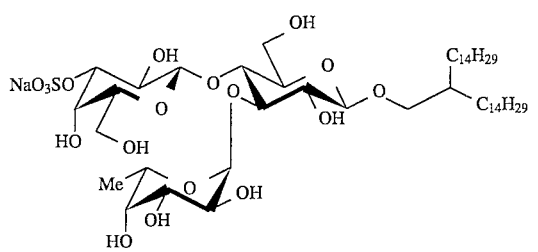
(IIa)

The salt of glycolipid derivative of Formula (I) may be synthesized by reacting the polysaccharide derivative of Formula (III):

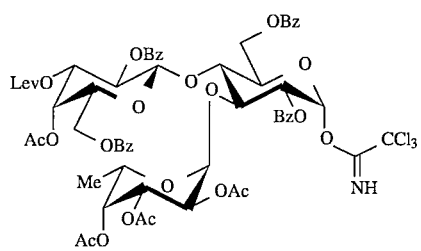
(III)

wherein all symbols are as defined, with an alcohol of Formula (IV):

HO—R      (IV)

wherein R is as defined, eliminating the levuloyl group followed by sulfating, eliminating the acetyl and benzoyl groups, and converting the free acid to a desired salt.

A method of synthesis of the compound of Formula (IIa) is described below in detail for exemplifying purposes. It will be easily appreciated, however, that other specific compounds encompassed within the present invention may be prepared in an analogous manner. The method starts from the compound of Formula (III). In the first step, the starting material (III) is reacted with 2-(tetradecyl)hexadecanol of Formula (V):

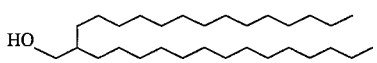
(V)

in dichloromethane in the presence of boron trifluoride-ether complex. The next step includes elimination of levuloyl group from the product by the reaction with hydrazine monoacetate in ethanol followed by sulfating with sulfur trioxide-pyridine complex in DMF. Finally acetyl and benzoyl groups are eliminated from the reaction product by subjecting to the reaction with sodium methoxide in a mixture of methanol and THF. The compound of Formula (IIa) and intermediates formed in various steps may be isolated by any conventional method such as silica gel chromatography.

The starting material (III) may be prepared, in turn, according to the following reaction scheme:

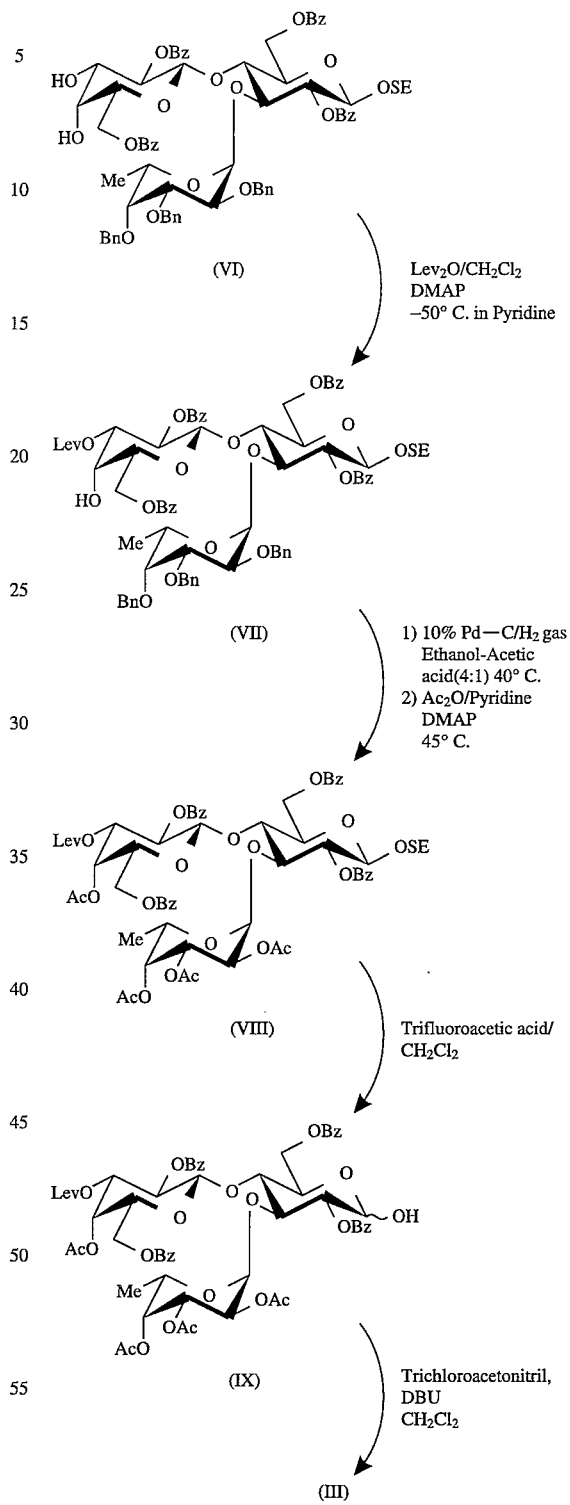

In the above formulas, various symbols have the following meaning:
Bn=benzyl;

DMAP=4-dimethylaminopyridine;
DBU=1,8-diazabicyclo [5.4.0]-7-undecene;
SE=2-(trimethylsilyl)ethyl;
Lev$_2$O=levulinic anhydride; and
Ac$_2$O=acetic anhydride.

Ac, Bz and Lev are as defined.

Briefly, compound (VI) [J. Carbohydrate Chem., 12, 1203–1216 (1993)] is reacted with levulinic anhydride in the presence of 4-dimethylaminopyridine to protect the 3-hydroxyl group of the galactose moiety thereof with levuloyl whereupon compound (VII) is obtained.

Next, compound (VII) is catalytically hydrogenated in the presence of palladium-carbon to eliminate benzyl groups and then reacted with acetic anhydride in pyridine to produce compound (VIII).

Compound (VIII) is then reacted with trifluoroacetic acid to eliminate the 2-(trimethylsilyl)ethyl group whereupon compound (IX) is produced.

Finally, compound (IX) is reacted with trichloroacetonitrile in the presence of 1,8-diazabicyclo [5.4.0]-7-undecene to produce compound (III).

2-(tetradecyl)hexadecanol (V) may be produced from 2-(tetradecyl)hexadecanoic acid by esterifying with methanol in the presence of a small amount of concentrated sulfuric acid followed by reduction with lithium aluminum hydride.

pharmaceutical compositions containing a salt of the glycolipid derivative of Formula (I) may be administered orally or parenterally. The dose will vary depending upon the administration route, the age, body weight and severity of disease of the patient, and generally ranges from 0.1 to 600 mg/day. This dose may be administered at once or in divided doses two to four times a day.

Pharmaceutical formulations for oral administration include tablets, granules, powder, fine granules and capsules. Tablets, granules, powder and fine granules are made by mixing the active ingredient with a pharmaceutically acceptable carrier such as an excipient (lactose, synthetic aluminum silicate, glucose, mannitol, crystalline cellulose, starch etc.,), a disintegrating agent (CMC, sodium alginate etc.,), a lubricant (magnesium stearate, talc etc.,), and/or a binder (hydroxymethylcellulose, hydroxypropylmethylcellulose, polyvinylpyrrolidone etc.,), and then, if necessary forming the mixture into the desired formulation. Capsules are made by filling a capsule with the above granules or powder.

Injectable liquid formulations may be made by dissolving or dispersing a pharmaceutically acceptable salt of the glycolipid derivative of Formula (I) in sterile water, adding a suitable amount of an isotonic agent such as mannitol, sodium chloride, glucose, sorbitol, glycerol, xylitol, fructose, maltose or mannose, and then sterile sealing in an vial or ampoule. The injectable formulation may optionally contain a stabilizing agent such as sodium sulfite or albumin and a preversative such as benzyl alcohol.

The compounds of the present invention exert a strong inhibitory effect on the binding of E-, P- or L-selectin to sialyl Lewis$^x$ and exhibit a low toxicity. In an in vivo test using mice having inflammatory cell invasion induced by a lipopolysaccharide, the compounds of the present invention demonstrated a remarkable inhibitory activity against inflammatory cell invasion when administered intravenously. In the in vitro test described below, the compounds of the present invention inhibited the binding of selectin family to sialyl Lewis$^x$ in a dose response manner. This suggests that the compounds of the present invention would be useful in the prophylaxis and treatment of complicated inflammatory disease such as chronic inflammation and also in the prophylaxis and treatment of ischemia-reperfusion injury because selectin-mediated cell adhesion would be prevented by binding the compounds of the present invention to the selectin family.

Test No.1

Inhibition of P-selectin-sialyl Lewis$^x$ binding (1) Test Compound:

Sodium salt of 2-(tetradecyl)hexadecyl O-(3-O-sulfo-β-D-galactopyranosyl)-(1→4)-O-[α-L-fucopyranosyl)-(1→3)-]-α-D-glucopyranoside (Example 2).

(2) Method:

The method using selectin-IgG chimeras reported by Foxall et al., in J. Cell Biol., 117, 895–902 (1992) was followed.

A solution of sialyl Lewis$^x$-penta-ceramide in 1:1 mixture of methanol and distilled water was pipetted into microtiter plate wells (96 wells) at 200 pmol/well and adsorbed by evaporating the solvent. The wells were washed with distilled water, blocked with 5% BSA (bovine serum albumin) -PBS (phosphate buffered saline) for 1 hour and washed again with distilled water after discarding the blocking solution.

Separately, a 1:1 volumetric mixture of 1:1000 dilution in 1% BSA-PBS of horseradish peroxidase-labelled anti-human IgG Fc and a culture supernatant containing P-selectin IgG chimera was incubated at room temperature for 30 minutes to form a complex. The test compound was dissolved in distilled water at 0.1 mM and finally diluted to final concentrations at 100, 25, 6.25 and 1.56 μM, respectively. Reactant solutions were prepared by incubating this solution at each concentration with the above complex solution for 30 minutes at room temperature. This reactant solution was then added to the above microtiter wells at 50 μl/well and allowed to react at room temperature for 2 hours. The wells were washed thrice with PBS and distilled water respectively, and developed for 10 minutes by adding 0.2 mg/ml of o-phenylenediamine and 0,015% of H$_2$O$_2$ in 0.05M citrate-phosphate buffer (pH 9.5) at 50 μl/well. The reaction was stopped by the addition of 2N sulfuric acid at 50 μl/well and absorbance at 490 nm was measured. Percent binding was calculated by the following equation:

$$\% \text{ Binding} = (X/A) \times 100$$

wherein X is the absorbance of wells containing the test compound at each concentration, and A is the absorbance of control wells not containing the test compound.

(3) Results:

The results are shown in the graph of FIG. 1.

Test No. 2

Inhibition of L-selectin-sialyl Lewis$^x$ binding

Figure 2:
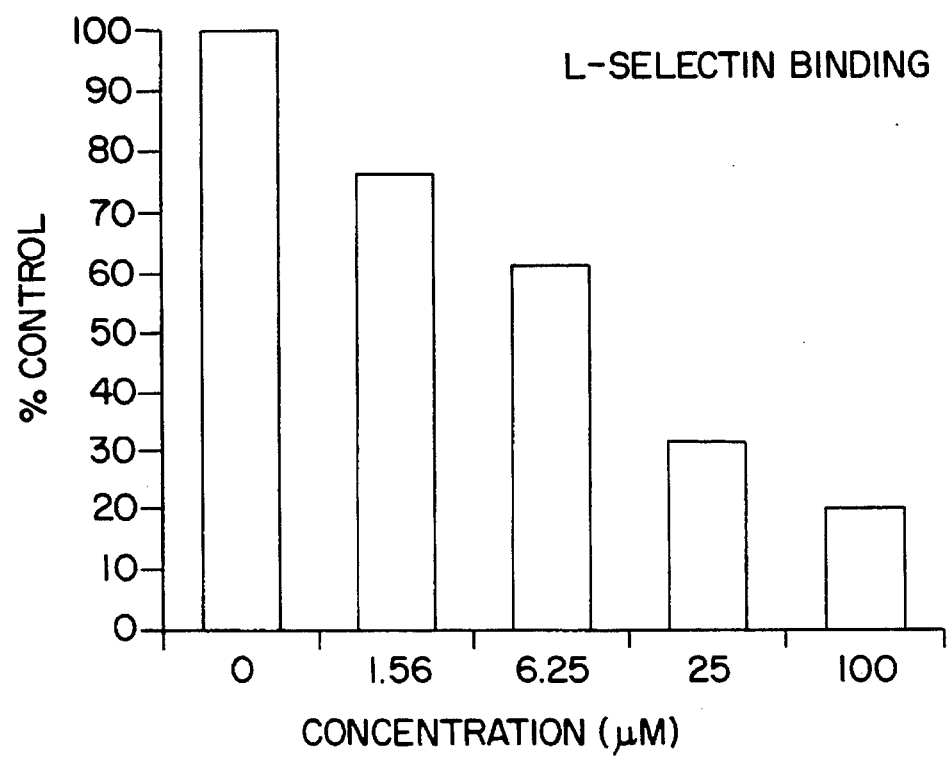
FIG. 2 is a graph similar to FIG. 1 showing the inhibitory effect of the glycolipid derivative of the present invention at varying concentrations on the binding of L-selectin to sialyl Lewis$^x$.

Test No. 1 was repeated except that L-selectin IgG chimera was replaced for P-selection IgG chimera. The results are shown in the graph of FIG. 2.

Reference Example 2-(Tetradecyl)hexadecanol (V)

144 mg of 2-(tetradecyl)hexadecanoic acid was dissolved in 25 ml of methanol. After the addition of a few drops of concentrated sulfuric acid, the solution was stirred at 55° C. for one day, neutralized with 10% sodium hydroxide and extracted with dichloromethane. The organic layer was washed with water, dried over anhydrous sodium sulfate and concentrated in vacuo. The residue was purified by silica gel chromatography (ethyl acetate:hexane=1:50) to obtain methyl 2-(tetradecyl)hexadecanoate.

290 mg of this methyl ester was dissolved in 25 ml of diethyl ether and cooled to 0° C. After the addition of an excess of lithium aluminum hydride, the solution was stirred at room temperature for one day. The reaction mixture was then mixed with 0.5 ml of water and filtered to remove insoluble matter. The filtrate was evaporated in vacuo and the residue purified by silica gel chromatography (ethyl acetate:hexane=1:20) whereupon 204.6 mg of the title compound was obtained.

EXAMPLE 1

(a) 2-(Trimethylsilyl)ethyl O-(2,6-di-O-benzoyl-3-O-levuloyl-β-D-galactopyranosyl)-(1→4)-O-[(2,3,4-tri-O-benzyl-α-L-fucopyranosyl-(1→3)]-O-2,6-di-O-benzoyl-β-D-glucopyranoside (VII)

450 mg of 2-(trimethylsilyl)ethyl O-(2,6-di-O-benzoyl-β-D-galactopyranosyl)-(1→4)-O-[(2,3,4-tri-O-benzyl-α-L-fucopyranosyl)-(1→3)]-O-2,6-di-O-benzoyl-β-D-glucopyranoside (VI)[J. Carbohydrate Chem., 12, 1203–1216 (1993)] was dissolved in a mixture of 5 ml of pyridine and 2 ml of dichloromethane. To this solution were added 150 mg of levulinic anhydride and 5 mg of 4-dimethylaminopyridine in 2 ml of dichloromethane while keeping the temperature at −50° C. After the addition, the mixture was stirred at the same temperature for 3 hours. After adding 1 ml of methanol the reaction mixture was evaporated in vacuo and extracted with dichloromethane. The extract was washed with 2M hydrochloric acid, 1M sodium carbonate and water successively. The organic layer was then dried over anhydrous sodium sulfate and evaporated in vacuo. The residue was purified by silica gel chromatography (ethyl acetate:hexane=1:3) whereupon 426 mg of the title compound (VII) was obtained. $[\alpha]_D$ −5.5° (c 0.9, $CHCl_3$)

$^1$H-NMR($CDCl_3$) δ: 1.44(m, 2H), 1.56(d, 3H, J=6.4 Hz), 2.33(s, 3H), 2.64, 2.90(m, 4H), 4.97(d, 1H, J=2:2 Hz), 5.04(dd, 1H, J=10.2, 3.1 Hz), 5.77(dd, 1H, J=7.9 Hz), 7.14–8.31(m, 35H). Analysis calculated for $C_{77}H_{84}O_{21}Si$: C 67.33, H 6.16; Found: C 67.33; H 6.00

(b) 2-(Trimethylsilyl)ethyl O-(4-O-acetyl-2,6-di-O-benzoyl-3-O-levuloyl-β-D-galactopyranosyl)-(1→4)-O-[(2,3,4-tri-O-acetyl-α-L-fucopyranosyl)-(1→3)]-O-2,6-di-O-benzoyl-β-D-glucopyranoside (VIII)

223 mg of compound (VII) in a mixture of 8 ml of ethanol and 2 ml of acetic acid was catalytically hydrogenated in the presence of 300 mg of 10% palladium-carbon at 45° C. for 12 hours. After the reaction, insoluble matter was filtered off from the reaction mixture and washed with ethanol. The filtrate was combined with the washing and evaporated in vacuo. The residue was then reacted with 2 ml of acetic anhydride in 3 ml of pyridine in the presence of 5 mg of 4-dimethylaminopyridine for 10 hours at room temperature with stirring. After adding 1 ml of methanol, the reaction mixture was extracted with dichloromethane and the extract washed with 2M hydrochloric acid, 1M sodium carbonate and water successively. The organic layer was dried over anhydrous sodium sulfate and evaporated in vacuo. The residue was applied on a silica gel column and eluated with a 1:3 mixture of ethyl acetate and hexane. 210 mg of the title compound (VIII) was obtained. $[\alpha]_D$−17.5° (c 1.0, $CHCl_3$)

$^1$H-NMR($CDCl_3$) δ: 0.89(m, 2H), 1.57(d, 3H, J=6.4 Hz), 2.06–2.42(5s, 15H), 2.56, 2.73(2m, 4H), 4.61(d, 1H, J=8.1 Hz), 5.26(dd, 1H, J=10.4, 3.7 Hz), 7.16–8.34(m, 20H). Analysis calculated for $C_{64}H_{74}O_{25}Si$: C 60.46; H 5.87; Found: C 60.33, H 5.75

(c) O-(4-O-acetyl-2,6-di-O-benzoyl-3-O-levuloyl-β-D-galactopyranosyl)-(1→4)-O-[(2,3,4-tri-O-acetyl-α-L-fucopyranosyl)-(1→3)]-O-2,6-di-O-benzoyl-β-D-glucopyranose (IX)

170 mg of compound (VIII) was dissolved in a mixture of 1 ml of dichloromethane and 2 ml of trifluoroacetic acid, and stirred at room temperature for 2 hours. After the addition of 1 ml of ethyl acetate, the solution was evaporated in vacuo. The residue was applied on a silica gel column and eluated with a 1:2 mixture of ethyl acetate and hexane. 144 mg of the title compound (IX) was obtained. $[\alpha]_D$+11.2° (c 0.8, $CHCl_3$)

$^1$H-NMR($CDCl_3$) δ: 1.26(d, 3H, J=7.1 Hz), 1.64–2.17(5s, 15H), 2.33, 2.53(2m, 4H), 4.11(d, 1H, J=7.2 Hz), 5.22(d, 1H, J=3.1 Hz), 5.73(d, 1H, J=2.7 Hz), 7.16–8.10(m, 20H). Analysis calculated for $C_{59}H_{62}O_{25}$: C 60.51; H 5.34; Found: C 60.27; H 5.08

(d) O-(4-O-acetyl-2,6-di-O-benzoyl-3-levuloyl-α-D-galactopyranosyl)-(1→4)-O-[(2,3,4-tri-O-acetyl-α-L-fucopyranosyl)-(1→3)]-O-2,6-di-O-benzoyl-β-D-glucopyranosyl-trichloroacetimidate (III)

To a solution of 653 mg of compound (IX) in a mixture of 9 ml of dichloromethane and 1.8 ml of trichloroacetonitrile was added 41.8 µl of 1 of 1,8-diazabicyclo [5.4.0]-7-undecene. The mixture was stirred at 0° C. for 2 hours and then evaporated in vacuo. The residue was applied on a silica gel column and eluated with a 1:2 mixture of ethyl acetate and hexane. 700 mg of the title compound (III) was obtained. $[\alpha]_D$+57° (c 1.4, $CHCl_3$)

$^1$H-NMR($CDCl_3$) δ: 1.40(d, 3H, J=6.1 Hz), 1.71–2.17(5s, 15H), 2.37, 2.53(2m, 4H), 4.83(d, 1H, J=8.3 Hz), 5.26(dd, 1H, J=3.7, 10.4 Hz), 5.35(dd, 1H, J=2.9, 11.0 Hz), 5.65(dd, 1H), 5.75(d, 1H), 6.48(d, 1H, J=3.7 Hz), 7.38–8.09(m, 20H), 8.46(s, 1H). Analysis calculated for $C_{61}H_{62}Cl_3NO_{25}$: C 55.69; H 4.75; N 1.06; Found:C 55.58; H 4.67; N 1.09

EXAMPLE 2

(a) 2-(Tetradecyl)hexadecyl O-(4-O-acetyl-2,6-di-O-benzoyl3-O-levuloyl-β-D-galactopyranosyl)-(1→4)-O-[(2,3,4-tri-O-acetyl-β-L-fucopyranosyl)-(1→3)]-O-2,6-di-O-benzoyl-β-D-glucopyranoside 700 mg of compound (III) produced in Example 1 and 363 mg of 2-(tetradecyl)hexadecanol (v) produced in Reference Example were dissolved in 8.8 ml of dichloromethane. After the addition of 1.7 g of molecular sieve(MS-4A), the solution was stirred at room temperature for 6 hours and then cooled at 0° C. To this was added 0.13 ml of boron trifluoride-ether complex followed by stirring at room temperature for 5 hours. The reaction mixture was filtered to remove insoluble matter which was then washed with dichloromethane. The filtrate was combined with this washing, and washed with 1M sodium carbonate and water successively. The organic layer was dried on anhydrous sodium sulfate and evaporated in vacuo. The residue was applied on a silica gel column and eluated with a 1:4 mixture of ethyl acetate and hexane. 585 mg of the title compound was obtained. $[\alpha]_D$−67.7° (c 1.0, $CHCl_3$)

$^1$H-NMR($CDCl_3$) δ: 0.88–1.43(m, 58H), 1.82–2.15(5s, 15H), 2.34, 3.67(2dd, 2H, J=9.3 Hz), 4.37(d, 1H, J=8.1 Hz), 4.79(d, 1H, J=8.2 Hz), 5.22(dd, 1H, J=3.8, 10.4 Hz), 5.47(d, 1H, J=2.8 Hz), 5.53(dd, 1H), 5.72(dd, 1H, 7.35–8.13(m, 20H). Analysis calculated for $C_{89}H_{122}O_{25}$: C 67.15; H 7.72; Found: C 67.11; H 7.67

(b) 2-(Tetradecyl)hexadecyl O-(4-O-acetyl-2,6-di-O-benzoyl-β-D-galactopyranosyl)-(1→4)-O-[2,3,4-tri-O-acetyl-α-L-fucopyranosyl)-(1→3)]-O-2,6-di-O-benzoyl-β-D-glucopyranoside To a solution of 583.5 mg of the product of step (a) in 15 ml of ethanol was added 168 mg of hydrazine monoacetate and mixture stirred at room temperature for 1 hour. The reaction mixture was then evaporated in vacuo. The residue was applied on a silica gel column, and eluated with a 1:3 mixture of ethyl acetate and hexane. 545 mg of the title compound was obtained. $[\alpha]_D$−24.7° (c 1.0, $CHCl_3$)

$^1$H-NMR(CDCl$_3$) δ: 0.85–1.33(m, 58H), 1.59–2.11(4s, 12H), 3.09, 3.79(2dd, 2H, J=9.3 Hz), 4.38(d, 1H, J=7.7 Hz), 4.63(bs, 1H), 4.67(d, 1H, J=8.6 Hz), 5.60(d, 1H, J=2.9 Hz), 7.33–8.15(m, 20H). Analysis calculated for C$_{84}$H$_{116}$O$_{23}$: C 67.54; H 7.83; Found: C 67.30; H 7.53

(c) Pyridine salt of 2-(tetradecyl)hexadecyl O-(4-O-acetyl2, 6-di-O-benzoyl-3-O-sulfo-β-D-galactopyranosyl)-(1→4)-O-[(2,3,4-tri-O-acetyl-α-L-fucopyranosyl)-(1→3)]-O-2,6-di-O-benzoyl-β-D-glucopyranoside To a solution of 78 mg of the product of step (b) in 1 ml of DMF was added 41 mg of sulfur trioxide-pyridine complex followed by stirring at room temperature for 1 hour. After the addition of 0.5 ml of methanol, the reaction mixture was evaporated at 25° C. The residue was applied on a silica gel column and eluated with a 20:1 mixture of dichloromethane and methanol. 75 mg of the title compound was obtained. [α]$_D$–2.2° (c 1. 0, CHCl$_3$)

$^1$H-NMR(CDCl$_3$) δ: 0.85–1.31(m, 58H), 1.38(d, 3H, J=6.2 Hz), 1.74–2.35(4s, 12H), 4.37(d, 1H, J=7.7 Hz), 7.09–8.05(m, 25H).

(d) Sodium salt of 2-(tetradecyl)hexadecyl O-(3-O-sulfo-β-D-galactopyranosyl)-(1→4)-O-[α-L-fucopyranosyl)-(1→3)]-β-D-glucopyranoside (IIa)

To a solution of the product of step (c) in a mixture of 2 ml of methanol and 1 ml of THF was added 5 mg of sodium methoxide followed by stirring at room temperature for 24 hours. The reaction mixture was evaporated at 25° C. The residue was applied on a column of Sephadex LH-20 and eluated with a 5:4:0.7 mixture of chloroform, methanol and water. 42 mg of the title compound (IIa) was obtained. [α]$_D$–30° (c 0.8, CHCl$_3$:MeOH=1:1)

$^1$H-NMR(C$_5$D$_5$N) δ: 0.85–1.31(m, 58H), 1.54(d, 3H, J=6.41 Hz), 5.06(d, 1H, J=2.71 Hz), 5.21(dd, 1H, J=3.8, 10.1 Hz), 5.41(d, 1H, J=7.3 Hz), 5.48(d, 1H, J=6.7 Hz).

Mass spectrum (m/e):989.7 (M+2H) Analysis calculated for C$_{48}$H$_{91}$SNa: C 57.01; H 9.07; Found: C 56.70; H 8.81

EXAMPLE 3

A mixture of 100 wt. parts of compound (IIa) produced in Example 2, 30 wt. parts of lactose, 20 wt. parts of crystalline cellulose, 5 wt. parts of hydroxypropylmethylcellulose and 20 wt. parts of CMC was thoroughly kneaded with 150 wt. parts of distilled water. The resulting mass was crushed into coarse particles and dried. After the addition of 5 wt. parts of magnesium stearate, the particles were compressed into tablets each having a diameter of 8 mm and a weight of 180 mg. The tablets contain the active ingredient at 100 mg/tablet.

EXAMPLE 4

0.5 wt. parts of the compound (IIa) of Example 2 and 5 wt. parts of sorbitol were dissolved in distilled water to make 100 wt. parts of a solution. Then, the solution was filtered through a membrane filter, packaged in nitrogen gas-filled fused ampoules at 5 ml/ampoule, and steam sterilized at 120° C. for 15 minutes. Each ampoule contains 25 mg of the compound (IIa).

We claim:

1. A glycolipid derivative of Formula (I):

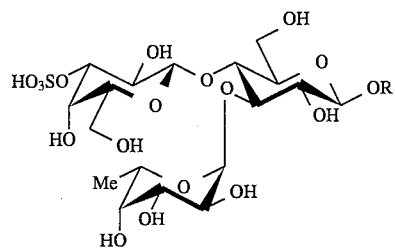

wherein R is 2-(tetradecyl) hexadecyl, in the form of a pharmaceutically acceptable salt.

2. The glycolipid derivative of claim 1, wherein said pharmaceutically acceptable salt is sodium, potassium, calcium, magnesium, arginine or lysine salt.

3. The glycolipid derivative of claim 1 having Formula (IIa):

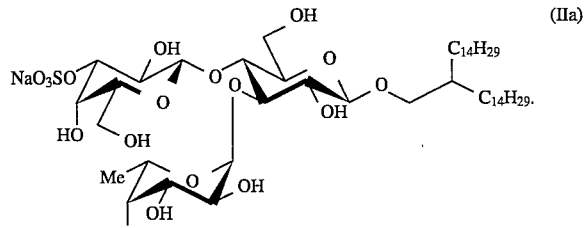

4. A compound of Formula (III):

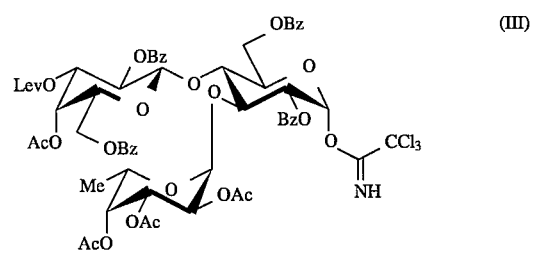

wherein Ac is acetyl, Bz is benzoyl, and Lev is levuloyl.

5. A pharmaceutical composition comprising a pharmaceutically acceptable salt of a glycolipid derivative of Formula (I):

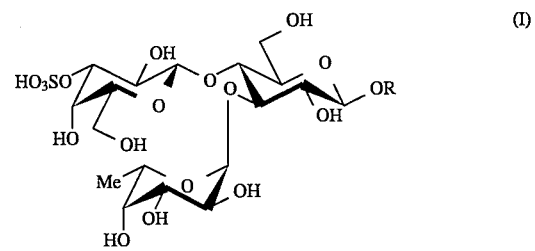

wherein R is 2-(tetradecyl) hexadecyl, in admixture with a pharmaceutically acceptable carrier.

6. The pharmaceutical composition of claim 5, wherein said pharmaceutically acceptable salt is sodium, potassium, calcium, magnesium, arginine or lysine salt.

7. The pharmaceutical composition of claim 5, wherein said pharmaceutically acceptable salt has Formula (IIa):

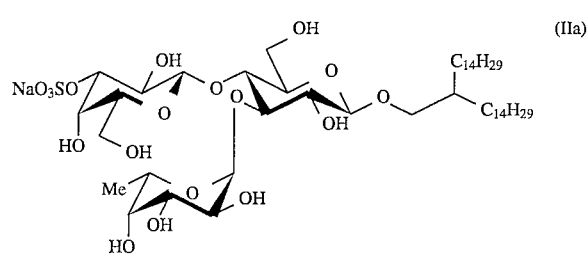
(IIa)
8. The pharmaceutical composition of claim 5 formulated for oral administration and in the form of tablets, granules, powder or capsules.
9. The pharmaceutical composition of claim 5 formulated for parenteral administration and in the form of a sterile isotonic solution.
* * * * *